(12) United States Patent
Humes et al.

(10) Patent No.: US 7,874,998 B2
(45) Date of Patent: Jan. 25, 2011

(54) FILTRATION DEVICES AND RELATED METHODS THEREOF

(75) Inventors: H. David Humes, Ann Arbor, MI (US); David L. Brown, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 870 days.

(21) Appl. No.: 11/593,270

(22) Filed: Nov. 6, 2006

(65) Prior Publication Data
US 2008/0004712 A1 Jan. 3, 2008

Related U.S. Application Data

(60) Provisional application No. 60/733,375, filed on Nov. 4, 2005.

(51) Int. Cl.
*A61M 37/00* (2006.01)
*C02F 1/44* (2006.01)
*C12N 5/00* (2006.01)
*C12N 5/017* (2006.01)

(52) U.S. Cl. ............... 604/5.04; 604/4.01; 210/645; 210/646; 435/372; 435/400

(58) Field of Classification Search .......... 604/4.01, 604/5.01, 5.04, 6.09, 6.11, 8, 9; 210/645, 210/646, 195.2, 321.79; 435/366, 369, 372, 435/400
See application file for complete search history.

(56) References Cited

U.S. PATENT DOCUMENTS

| | | |
|---|---|---|
| 3,370,710 A | 2/1968 | Bluemle |
| 3,373,876 A | 3/1968 | Stewart |
| 3,505,686 A | 4/1970 | Bodell |
| 3,704,223 A | 11/1972 | Dietzch et al. |
| 3,864,259 A | 2/1975 | Newhart |
| 3,884,808 A | 5/1975 | Scott |
| 4,176,069 A | 11/1979 | Metz et al. |
| 4,354,933 A | 10/1982 | Lester |
| 4,913,702 A | 4/1990 | Yum et al. |
| 4,929,233 A | 5/1990 | Roth et al. |
| 4,946,456 A | 8/1990 | Roth et al. |
| 5,024,663 A | 6/1991 | Yum |
| 5,549,674 A * | 8/1996 | Humes et al. ............ 623/23.65 |
| 6,150,164 A | 11/2000 | Humes |
| 6,213,973 B1 | 4/2001 | Eliasen et al. |
| 6,561,996 B1 * | 5/2003 | Gorsuch ................ 604/6.09 |
| 6,632,217 B2 | 10/2003 | Harper et al. |
| 6,913,588 B2 | 7/2005 | Weitzel et al. |
| 7,407,499 B2 | 8/2008 | Trautman |

(Continued)

OTHER PUBLICATIONS

Birla et al., "Myocardial engineering in vivo: formation and characterization of contractile, vascularized three-dimensional cardiac tissue", 2005, Tissue Engineering, 11(5-6):803-13.

(Continued)

*Primary Examiner*—Leslie R Deak
(74) *Attorney, Agent, or Firm*—Casimir Jones SC

(57) ABSTRACT

The present invention relates to filtration devices and related methods of use. In particular, the present invention relates to implantable filtration devices used, for example, for filtering impurities from a body fluid of a subject.

6 Claims, 12 Drawing Sheets

U.S. PATENT DOCUMENTS

2010/0267136 A1* 10/2010 Vacanti et al. .............. 435/366

OTHER PUBLICATIONS

Brenner and Humes, "Mechanics of glomerular ultrafiltration", 1977, New Engl J Med, 297:148-154.

Brenner et al., "Molecular basis of proteinuria of glomerular origin", 1978, New Engl J Med, 298:826-833.

Chang et al., "Permselectivity of the glomerular capillary wall to macromolecules. I. Theoretical considerations", 1975, Biophys J, 15:861.

Colton et al., "Kinetics of hemodiafiltration. I. In vitro transport characteristics of a hollow-fiber blood ultrafilter", 1975, J Lab Clin Med, 85:355-371.

Erol and Sira, "New capillary bed formation with a surgically constructed arteriovenous fistula", 1980, Surgery, 66:109-115.

Excerpts from United States Renal Data System 1991 Annual Data Report, 1991, Am J Kidney Diseases, 18(5): Supplement 2:21-30.

Folkman and Shing, "Angiogenesis", 1992, Angiogenesis J Biol Chem, 267(16):10931-10934.

Golper, "Continuous arteriovenous hemofiltration in acute renal failure", 1985, Am J Kidney Diseases, 6:373-386.

Henderson et al., "Kinetics of hemodiafiltration. II. Clinical characterization of a new blood cleansing modality", 1975, J Lab Clin Med, 85:372-391.

Iglehart, "The American health care system. The End Stage Renal Disease Program", 1993, New Engl J Med, 328:366-371.

Ingber and Folkman, "Mechanochemical switching between growth and differentiation during fibroblast growth factor-stimulated angiogenesis in vitro: role of extracellular matrix", 1989, J Cell Biol, 109:317-330.

Kadletz et al., "Implantation of in vitro endothelialized polytetrafluoroethylene grafts in human beings. A preliminary report", 1992, J Thorac Cardiovasc Surg, 104:736-42.

Khouri et al., "Tissue generation with growth factors", 1993, Surgery, 114:374-380.

Kramer et al., "[Arteriovenous haemofiltration: a new and simple method for treatment of over-hydrated patients resistant to diuretics] [Article in German]", 1977, Klin Wochenschr, 55:1121-1122.

Madri et al., "Phenotypic modulation of endothelial cells by transforming growth factor-beta depends upon the composition and organization of the extracellular matrix", 1988, J Cell Biol, 106:1375-1384.

Mian et al., "Formation of new tissue from an arteriovenous loop in the absence of added extracellular matrix", 2000, Tissue Engineering, 6(6):595-603.

Richardson et al., "Polymeric system for dual growth factor delivery", 2001, Nat Biotechnol, 19:1029-1034.

Schneider et al., "Durability of confluent endothelial cell monolayers on small-caliber vascular prostheses in vitro", 1988, Surgery, 103:456-462.

Shepard et al., "Endothelial cell seeding of small-caliber synthetic grafts in the baboon",1986, Surgery 99:318-325, 986.

Tanaka et al., "Tissue engineering skin flaps: which vascular carrier, arteriovenous shunt loop or arteriovenous bundle, has more potential for angiogenesis and tissue generation?", 2003, Plast Reconstr Surg, 112(6):1636-44.

Tanaka et al., 1996, Jpn PRS, 16:679-686.

Thompson et al., "Site-directed neovessel formation in vivo", 1988, Science, 241:1349-1352.

Yancopoulos et al., "Vascular-specific growth factors and blood vessel formation", 2000, Nature, 407:242-248.

* cited by examiner

AB

CD

Group 1

Group 2

Group 3

FILTRATION DEVICES AND RELATED METHODS THEREOF

This application claims priority to U.S. Provisional Application Ser. No. 60/733,375, filed Nov. 4, 2005, which is herein incorporated by reference in its entirety.

This invention was made with government support under W81XWH-05-2-0010 awarded by the Army Medical Research and Material Command. The government has certain rights in the invention.

FIELD OF THE INVENTION

The present invention relates to filtration devices and related methods of use. In particular, the present invention relates to implantable filtration devices used, for example, for filtering impurities from a body fluid of a subject.

BACKGROUND

The excretory function of the kidney, the formation of urine, begins in the kidney with filtration of blood at the glomerulus which is a tuft of capillaries. These capillaries invaginate a surrounding capsule called Bowman's capsule where the renal tubule system begins. The structure of the glomerulus is designed to provide efficient ultrafiltration of blood to remove toxic wastes from the circulation and retain important components within the systemic circulation, such as albumin (see, e.g., Brenner and Humes, New Engl. J. Med. 297:148-154, 1977; Brenner et al., New Engl. J. Med. 298: 826-833, 1978; both incorporated herein by reference in their entireties).

The regulatory function of the kidney, especially with regard to fluid and electrolyte homeostasis, is provided by the tubular segments attached to the glomerulus. It is in the renal tubules where processes of osmosis, diffusion as well as active transport all assist in converting glomerular filtrate into urine. The ultrafiltrate emanating from the glomerulus courses along the kidney tubule which reabsorbs fluid and solutes to finely regulate the excretion of various amounts of solutes and water in the final urine. The functional unit of the kidney is, therefore, composed of the filtering unit, the glomerulus, and the regulatory unit, the tubule. Together they form the basic component of the kidney, called the nephron.

End stage renal disorder (ESRD) is a common clinical syndrome involving a decline in renal function, either acutely or chronically. The clinical manifestations of this disorder arise from a decrease in the glomerular filtration rate and an inability of the kidney to excrete the toxic metabolic wastes produced by the body. The complete treatment of ESRD is dependent upon the replacement of the filtrative, reabsorptive, homeostatic and endocrine functions of the kidney as an integrated organ structure.

Hemodialysis and chronic ambulatory peritoneal dialysis (CAPD) involves long-term ex vivo replacement therapy for support of renal function (see, e.g., Iglehart, N. Engl. J. Med. 328:366-371, 1993; Excerpts from United States Renal Data System 1991 Annual Data Report. Am. J. Kidney Diseases 18(5) Supplement 2:21-30, November, 1991; herein incorporated by reference in its entirety). Conventional hemodialysis for ESRD mimics to some extent the filtration function of the kidney by circulating a patient's blood through or over a dialysate solution physically separated from the blood by a porous or permeable wall or membrane. The process results in the preferential diffusion of small molecules, such as urea, from the bloodstream into the dialysate solution. Examples of some hemodialyzers and their function are described, for example, in U.S. Pat. Nos. 3,370,710; 3,373,876; 3,505.686; 3,704,223; 3,864,259; 3,884,808; 4,176,069 and 4,354,933; each herein incorporated herein by reference in their entireties.

Although hemodialysis adequately removes small molecules from the bloodstream, no method has been established which provides for selectively removing or retaining larger molecules. Furthermore, dialysate solutions must be carefully controlled to ensure that their concentrations of biologically essential materials (such as inorganic salts and glucose) are balanced so that these materials which are present in the blood are retained by the blood. There is a strong need for improvements over existing systems.

Organ transplantation is also a limited therapeutic option due to the lack of available organs, the obligatory immunosuppressant medication that must be taken, and the high risk for tissue rejection.

What are needed are viable alternatives to dialysis and organ transplantation for treating kidney failure and kidney disease. In particular, artificial devices the mimic one or more functions of kidneys are needed that are configured for implantation into a patient. Ideally, such devices are configured for extended placement in the patient.

SUMMARY OF THE INVENTION

The present invention relates to filtration devices and related methods of use. In particular, the present invention relates to implantable filtration devices used, for example, for filtering impurities from a body fluid of a subject. Generally, kidney failure is treated with kidney dialysis and/or kidney transplantation. The present invention, however, provides devices capable, for example, of filtering a subject's blood without the risk of organ transplantation or kidney dialysis.

The present invention provides filtration devices configured for implantation into a subject such that a tissue flap or AV loop is positioned within the device resulting in maintained neovasculature within the device. In experiments conducted during the course of the present invention, the devices of the present invention were shown to engage vascular tissue resulting in the formation of capillary beds within the device. Additionally, the devices were shown to achieve small solute clearance while maintaining permselectivity to large serum proteins. Additionally, experiments conducted during the course of the present invention indicated that the use of angiogenic growth factors (e.g., angiogenin, angiopoietin-1, del-1, fibroblast growth factors: acidic (aFGF) and basic (bFGF), follistatin, granulocyte colony-stimulating factor (G-CSF), hapatocyte growth factor (HGF)/scatter factor (SF), interleukin-8 (IL-8), leptin, midkine, placental growth factor, platelet-derived endothelial cell growth factor (PD-ECGF), platelet-derived growth factor (VDGF), platelet-derived growth factor-BB (PDGF-BB), pleiotrophin (PTN), proliferin, transforming growth factor-alpha (TGF-alpha), transforming growth factor-beta (TGF-beta), tumor necrosis factor-alpha (TNF-alpha), and vascular endothelial growth factor (VEGF)/vascular permeability factor (VPF)) within the devices (e.g., within the housing of the devices) enhanced capillary bed formation within the devices, thereby improving, for example, the effectiveness of the devices. The devices of the present invention are not limited to any particular purpose or use. Indeed, the devices of the present invention may be used in a wide array of applications including, but not limited to, research based applications, drug screening applications, and/or therapeutic applications.

In certain embodiments, the present invention provides a device configured for implantation into a living organism, the device comprising a housing having therein at least one opening, the housing configured to engage vascular tissue through the at least one opening such that an engagement results in the formation of a capillary bed within the housing, the housing having therein a plurality of semi-permeable hollow fibers connected to a conduit, the plurality of semi-permeable hollow fibers configured to remove impurities from blood and pass the removed impurities into the conduit.

In some embodiments, the at least one opening is a circular opening. In some embodiments, the at least one opening is an extended slit running the length of the housing.

In some embodiments, the housing has therein growth factors for enhancing capillary bed formation within the housing. The device is not limited to a certain amount of growth factors or type of growth factors or means for delivering growth factors to the housing. In some embodiments, the growth factors are delivered to the housing over an extended period of time (e.g., timed release). In some embodiments, the growth factors are delivered to the housing via an osmotic pump (e.g., an Alzet osmotic pump 2004). In some embodiments, the growth factors include at least one growth factor, including, but not limited to platelet-derived growth factors, vascular endothelial growth factors, and fibroblast growth factors.

In some embodiments, the device further comprises a reservoir configured to receive the removed impurities from the conduit. In some embodiments, the device further comprises a vascular access port configured to access the reservoir.

In some embodiments, the vascular tissue is selected from the group consisting of femoral artery and femoral vein.

A wide variety of materials may be used for the composition of the housing, including but not limited to, plastic, metal, ceramic, and mixtures thereof. In some embodiments, the composition of the housing comprises platinum-cured silicone tubing. In some embodiments, the composition of the housing is polypropylene.

The present invention is not limited to a particular internal volume for the reservoir. In some embodiments, the internal volume of the reservoir is as small as, for example, 0.1 cc, 1 cc, 5 cc, 10 cc, 50 cc, 100 cc, and as large as, for example, 0.5 liters, 1 liter, 2 liters, 5 liters, and 10 liters. In some embodiments, the internal volume of the reservoir is approximately 0.35 cc. In some embodiments, the housing has an internal volume of from μL to multiple mL volumes.

In some embodiments, the filtration devices of the present invention are configured for long-term implantation in a patient (e.g., a week, a month, 3 months, 6 months, 9 months, 12 months, 2 years, etc.). In some embodiments, the filtration devices are configured to allow manipulation or replacement of components (e.g., reservoir replacement) without disturbing (e.g., leaving intact) the capillary beds formed within the housing. In some embodiments, the filtration devices further comprise imaging components, sensors, or detectable components that allow a physician to monitor or locate the device without surgically opening a patient.

In some embodiments, the vascular access point is configured for removal of the impurities collected in the reservoir.

In some embodiments, the vascular tissue is an AV loop between the femoral artery and femoral vein of the living organism. In some embodiments, the vascular tissue is a tissue flap. In some embodiments, the vascular tissue is another vascular bed, including but not limited to the iliac artery or iliac vein of the living organism.

In certain embodiments, the present invention provides a method of treating renal failure in a living organism, comprising placement of a filtration device of the present invention into a living organism such that the housing engages vascular tissue. In some embodiments, the impurities collected with the filtration device are removed through the vascular access point.

In certain embodiments, the present invention provides kits comprising filtration devices of the present invention.

GENERAL DESCRIPTION

Figure 1A:
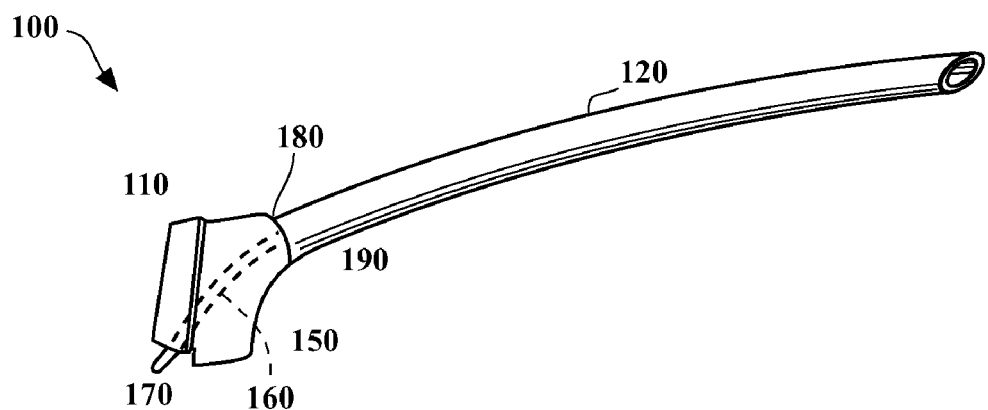
FIG. 1 shows a side view of a filtration device of the present invention.

Tissue engineering is a rapidly developing field in biotechnology. Tissue engineering refers to the design, modification, or replacement of specific tissues by manipulation of molecules, cells, or component structures to maintain, restore, or improve the function of a tissue. The kidney may be the initial solid organ in which tissue engineering is able to restore physiologic function for subjects suffering from end organ failure (see, e.g., Humes H D, Tissue engineering of the kidney. In: Bronzino J D, editor-in-chief. Biomedical Engineering Handbook. Boca Raton, Fla.: CRC Press, 1995; 1807-1824; herein incorporated by reference in its entirety).

The kidney was the first solid organ whose function was approximated by a machine and a synthetic device. Renal substitution therapy with hemodialysis or chronic ambulatory peritoneal dialysis has been the only successful long-term ex vivo organ substitution therapy to date (see, e.g., Iglehart J K, N Engl J Med 328:366, 1993; herein incorporated by reference in its entirety). The kidney was also the first organ to be successfully transplanted from a donor individual to an autologous recipient patient. However, the lack of widespread availability of suitable transplantable organs has kept kidney transplantation from becoming a practical solution in most cases of chronic renal failure.

Although long-term chronic renal replacement therapy with dialysis has dramatically changed the prognosis of renal failure, it is not a complete replacement therapy, since it only provides filtration function, usually on an intermittent basis, and does not replace the homeostatic, regulatory, metabolic, and endocrine functions of the kidney. Because of the nonphysiologic manner in which dialysis performs or does not perform the most critical renal functions, patients with end-stage renal disease (ESRD) on dialysis continue to have major medical, social, and economic problems (see, e.g., Excerpts from United States Renal Data System 1991 Annual Data Report. Prevalence and cost of ESRD therapy. Am J Kid Dis 18(5)(supp)2:21, 1991; herein incorporated by reference in its entirety).

Accordingly, the development of a bioartificial kidney comprised of synthetic and tubule cells to replace the full spectrum of kidney functions, including the filtration, reclamation, metabolic, and endocrine activities, will provide substantial benefits to the patient. These benefits would include increasing life expectancy, increasing mobility, improving quality of life while saving time required for treatment, and reducing the high cost of dialytic care.

In designing an implantable bioartificial kidney for renal replacement function, essential functions of kidney tissue should be considered to direct the tissue-engineering project. The critical elements of renal function should be replaced, including the excretory, regulatory (reabsorptive), and endocrinologic functions. The functioning excretory unit of the kidney is comprised of the filtering unit, the glomerulus, and the regulatory or reabsorptive unit, the tubule. Therefore, a bioartificial kidney provides two main units, the glomerulus and the tubule, to replace renal function.

The process of urine formation begins within the capillary bed of the glomerulus (see, e.g., Brenner B M and Humes H D, N Engl J Med 297:148, 1977; herein incorporated by reference in its entirety). The glomerular capillary wall has evolved into a structure with the property to separate as much as one-third of the plasma entering the glomerulus into a solution of a nearly ideal ultrafiltrate. This high rate of ultrafiltration across the glomerular capillary is a result of hydraulic pressure generated by the heart and the vascular tone of the preglomerular and postglomerular vessels as well as the high hydraulic permeability of the glomerular capillary walls. This hydraulic pressure and hydraulic permeability of the glomerular capillary bed is at least two times and two orders of magnitude higher, respectively, than most other capillary networks within the body (see, e.g., Landis E M and Pappenheimer J R. Exchange of substances through the capillary walls. In W F Hamilton, P Dow (eds), Handbook of Physiology: Circulation, sec 2, vol 2, p 961. Washington D.C.: American Physiological Society, 1963; herein incorporated by reference in its entirety). Despite this high rate of water and solute flux across the glomerular capillary wall, this same structure retards the filtration of important circulating macromolecules, including albumin, so that all but the lower-molecular-weight plasma proteins are restricted in their passage across this filtration barrier. A variety of experimental studies and model systems have been employed to characterize the sieving properties of the glomerulus. Hydrodynamic models of solute transport through pores have been successfully used to describe the size-selective barrier function of this capillary network to macromolecules (see, e.g., Brenner B M, et al., 1978, New Engl J Med 298: 826-833; herein incorporated by reference in its entirety). This modeling characterizes the glomerular capillary barrier as a membrane with uniform pores of 50-Å radius (see, e.g., Chang R L S, et al., 1975, Biophys J 15: 861; herein incorporated by reference in its entirety). Such a pore size model predicts that molecules with radii smaller than 14 Å will appear in the filtrate in the same concentration as in plasma water. The filtration of molecules of increasing size decreases progressively, so that the fractional clearance of macromolecules the size of serum albumin (e.g., approximately 36 Å) is low.

Accordingly, an important step in developing an implantable bioartificial kidney is to replace the hemofiltration function of the glomerular capillary bed. The potential for a bioartificial glomerulus has been achieved with the use of polysulphone fibers ex vivo with maintenance of convective ultrafiltration in humans for several days with a single device (see, e.g., Kramer P, et al., Klin Wochenschr 55:1121-1122, 1977; Golper T A, Am J Kidney Diseases 6:373-381, 1986; each herein incorporated by reference in their entireties). The availability of hollow fibers (semi-permeable hollow fibers) with high hydraulic permeability has been an important advancement in biomaterials for mimicking the convective filtration function of the glomerulus. Conventional hemodialysis for ESRD has used semi-permeable membranes in which solute removal is driven by a concentration gradient of the solute across the membranes and is therefore predominantly a diffusive process. Another type of solute transfer also occurs across the dialysis membrane via a process of ultrafiltration of water and solutes. This convective transport is independent of the concentration gradient and depends predominantly on the hydraulic pressure gradient across the membrane. Both diffusive and convective processes occur during traditional hemodialysis, but diffusion is the main route of solute movement. The development of synthetic membranes with high hydraulic permeability and solute retention properties in convenient semi-permeable hollow fiber form has promoted ESRD therapy based upon convective hemofiltration, similar to glomerular ultrafiltration, rather than diffusive hemodialysis (see, e.g., Colton C K, et al., J Lab Clin Med 85:355-371, 1975; Henderson L W, et al., J Lab Clin Med 85:372-391, 1975; each herein incorporated by reference in their entireties). The potential for an artificial glomerulus has been achieved with the use of polysulfone HFs ex vivo, with maintenance of convective ultrafiltration in humans, but only for several days with a single device (see, e.g., Kramer P, et al., 1977 Klin Wochenschr 55: 1121-1122; Golper T A, et al., 1986, Am J Kidney Dis 6: 373-381; each herein incorporated by reference in their entireties). Major limitations to the currently available synthetic membrane technology for long-term replacement of filtration function include, for example, bleeding associated with required anticoagulation and diminution of filtration rate due to protein deposition in the membrane or thrombotic occlusion.

One tissue engineering approach in developing a bioartificial implantable filtration device is to promote site-directed neovascularization in vivo (see, e.g., Thompson J A, et al., Science 241:1349-1352, 1988; herein incorporated by reference in its entirety). In this formulation, angiogenic growth factors can be delivered via exogenous administration to the internal compartments of the semi-permeable hollow fibers to induce targeted angiogenesis surrounding implanted semi-permeable hollow fibers (see, e.g., Folkman J and Shing Y. Angiogenesis. J Biol Chem 267(16):10931-10934, 1992; herein incorporated by reference in its entirety). These semi-permeable hollow fibers are envisioned to act as collecting conduits of ultrafiltrate produced by the newly-formed capillary network induced by the angiogenic factors. This formulation is based upon, for example, the intrinsic property inherent in all capillary beds to produce ultrafiltrate (see, e.g., Landis E M and Pappenheimer J R. Exchange of substances through the capillary walls. In W F Hamilton, P Dow (eds), Handbook of Physiology: Circulation, sec 2, vol 2, p 961. Washington D.C.: American Physiological Society, 1963; herein incorporated by reference in its entirety). This filtrate, or transudate, will collect in the semi-permeable hollow fiber network rather than the usual physiologic sites consisting of the interstitial space and lymphatics. The vectorial filtrate flow will be from capillary through interstitium into semi-permeable hollow fiber, since the hydraulic pressure difference from capillary lumen to semi-permeable hollow fiber will be greater than 20 mm Hg when the semi-permeable hollow fiber system is connected to its external drainage and collection system. The efficiency of this latter prototype depends upon the capillary density surrounding the semi-permeable hollow fiber bundles, which is dependent upon the efficacy of inducing targeted angiogenesis.

The use of endothelial cells seeded on the interior of the fiber conduits and filtration surfaces has been suggested as a means to provide improved long-term compatibility in vivo (see, e.g., Shepard et al., Surgery 99:318-325, 986; Kadletz et al., J. Thorac. Cardiovasc. Surg. 104:73642, 1992; Schneider et al., Surgery 103:456-462, 1988; each herein incorporated by reference in their entireties). In this regard, endothelial cell seeding of a small caliber vascular prosthesis has been shown experimentally to reduce long-term platelet deposition, thrombus formation and loss of graft patency. These constructs have been used solely as vascular conduits and not as filtering devices.

U.S. Pat. No. 5,549,674 describes a bioartificial filtration device comprising a chamber with at least one semi-permeable hollow fiber. The at least one semi-permeable hollow fiber has a coating of endothelial cells, epithelial cells, extracellular matrix, renal tubule cells, or a combination thereof. While endothelial cells in tissue culture have been shown to retain all the information necessary to develop three-dimensional capillary tube-like structures in vitro, the angiogenic potential is critically dependent upon both soluble and insoluble factors (see, e.g., Ingber D E and Folkman J., J Cell Biol 109:317-330, 1989; Madri J A, et al., J Cell Biol 106: 1375-1384, 1988; each herein incorporated by reference in their entireties).

U.S. Pat. No. 5,549,674 also describes a bioartificial filtration device comprising a plurality of semi-permeable hollow fibers designed for implantation in close proximity to a capillary network. A difficulty with this approach is that a new capillary bed can be promoted to develop in the proximity of the device, but the long-term maintenance and maturation of a neovascular bed has not been consistently achieved.

An approach to the formation of a persistent, mature, and long-term viable capillary bed provided by the present invention is the creation of tissue flaps. This approach is based upon the well-developed technique used in reconstructive surgery for the creation of skin flaps, a living viable construct of skin and its underlying tissue. These flaps retain their blood supply and maintain viability in the formation of new tissue. The development of a flap of viable tissue depends upon anatomically distinct blood vessel conduits. Tissue flaps can be constructed by implanting short segments of blood vessels into a desired site, and utilizing the resultant angiogenesis to influence neovascularization of a desired size and composition.

An extension of this technique has been demonstrated in experimental animals. The creation of an anastomosed arteriovenous (AV) loop beneath the skin produces a vascularized tissue flap (see, e.g., Erol O O and Spira M. Surgery 66:109-115, 1980; herein incorporated by reference in its entirety). Further refinements demonstrated that an AV loop can generate new, vascularized tissue when it is placed in collagenous matrix and isolated from the surrounding tissue within a plastic housing (see, e.g., Khouri R K, et al., Surgery 114: 374-380, 1993; Tanaka Y, et al., Jpn P.R.S. 16:679-686, 1996; each herein incorporated by reference in their entireties). These approaches, however, did not maintain long-term viability of tissue more than 30 days. The use of an empty plastic housing enclosing a surgically generated AV loop was more successful in developing a durable neovascular bed in a tissue flap filling the empty space of the implanted capsule (see, e.g., Rizwan M, et al., Tissue Engineering 6(6):595-603, 2000; herein incorporated by reference in its entirety).

A variation of this technique to produce a viable flap of tissue is to use an artery and vein as a vascular pedicle in which the blood vessels enter at one end of a semi-closed housing and exit at the opposite side. This axial-vascular design results, for example, in a well-vascularized flap of tissue (see, e.g., Tanaka Y, et al., Plast Reconstr Surg 112(6): 1636-44, 2003; Birla R K, et al., Tissue Engineering 11(5/6), 2005; each herein incorporated by reference in their entireties).

The efficiency of the filtration devices of the present invention are influenced by, for example, the capillary density surrounding the semi-permeable hollow fibers, which in turn is influenced by, for example, the efficacy of inducing targeted angiogenesis. In experiments conducted during the course of the present invention, angiogenic growth factors, including, but not limited to, vascular endothelial growth factors (VEGFs), angiopoietins, platelet-derived growth factor (PDGF), and fibroblast growth factors (FGFs) (see, e.g., Yancopoulos G D, et al., 2000, 407: 242-248; herein incorporated by reference in its entirety), were used to enhance capillary development within filtration devices.

The present invention provides filtration devices configured for implantation into a subject such that a tissue flap or AV loop is positioned within the device resulting in maintained neovasculature within the device. In experiments conducted during the course of the present invention, the devices of the present invention were shown to engage vascular tissue resulting in the formation of capillary beds within the device. Additionally, the devices were shown to achieve small solute clearance while maintaining permselectivity to large serum proteins. Additionally, experiments conducted during the course of the present invention showed that the use of angiogenic growth factors (e.g., VEGF, PDGF, FGF) within the devices (e.g., within the housing of the devices) enhanced capillary bed formation within the devices.

DETAILED DESCRIPTION

The present invention relates to filtration devices and related methods of use. In particular, the present invention relates to implantable filtration devices used, for example, for filtering impurities from a subject's bloodstream. FIGS. 1-14 illustrate various embodiments of the devices and related methods thereof. The present invention is not limited to these particular embodiments.

The embodiments describe the devices of the present invention in terms of nephrological applications (e.g., kidney disease, ESRD, malfunctioning kidney, dialysis). However, it should be appreciated that the devices are not limited to nephrological applications. Indeed, the devices of the present invention have application in any procedure requiring the formation of a vasculature bed within a particular location.

The filtration devices of the present invention comprise a device for purifying body fluids (e.g., blood and/or plasma) and suitably comprise either a single semipermeable hollow fiber or a collection of semi-permeable hollow fibers connected to a reservoir (described in more detail below). The filtration devices of the present invention promote ultrafiltration of blood via convective transport of water and solutes out of the blood and across the wall of the semi-permeable hollow fibers with high hydraulic permeability. Filtration of blood by a convective process has several distinct advantages: it imitates the glomerular process of toxin removal with increased clearance of higher molecular weight solutes and removes solutes up to a selected molecular weight cutoff at the same rate. Convective transport occurs independently of the existing concentration gradient and depends predominantly on the hydraulic pressure gradient across the membrane.

The filtration device can be suitably implanted either subcutaneously, on the peritoneal membrane, or within various tissues (such as muscle or kidney). Alternatively, the filtration device may be located outside the body. In some embodiments, the filtration device may be connected to other devices including but not limited to imaging devices (e.g., fiber-optic cameras), dialysis machines, a blood pump (e.g., Fresenius Model H Dialysis Machine Blood Pump (Fresenius Medical Care, Lexington, Mass.) and the Gambro Model AK-10 (Gambro Health Care, Stockholm, Sweden), and extracorporeal fluid circuits (e.g., U.S. Pat. No. 6,913,588; herein incorporated by reference in its entirety).

Figure 1B:
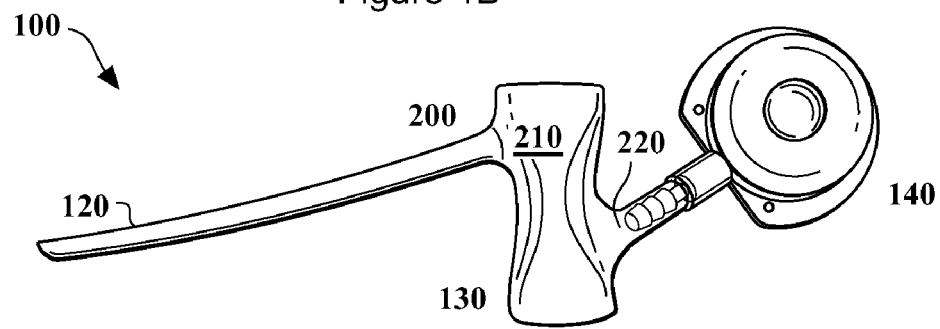

FIG. 1 shows a filtration device 100 of the present invention. In preferred embodiments, the filtration device 100 is configured to filter impurities from a subject's bloodstream in a manner similar to an operating kidney (described in more detail below). The filtration device 100 is not limited to particular size dimensions. In some embodiments, the size of the filtration device 100 is such that it is able to filter the blood of a small mammal (e.g., a rat). In some embodiments, the size of the filtration device 100 is such that it is able to filter the blood of a large mammal (e.g., gorilla, elephant, human).

Still referring to FIG. 1, the filtration device 100 generally comprises a housing 110, a conduit 120, a reservoir 130, and a vascular access port 140. In preferred embodiments, the filtration device 100 functions such that, following implantation into a subject, impurities (e.g., metabolic waste products) from a subject's blood flow into the housing 110 and are filtered into the reservoir 130 via the conduit 120, wherein the impurities may be collected via the vascular access port 140 (described in more detail below). The filtered blood is able to freely flow back into the subject's bloodstream.

Still referring to FIG. 1, the housing 110 is configured to receive blood, filter impurities from the blood, and pass the impurities into the conduit 120. The housing 110 is not limited to a particular size. In preferred embodiments, the size of the housing 110 is dependent upon the organism for which it is configured. For example, a housing 100 configured for a rat has dimensions of, for example, 4.8 mm ID, 6.4 mm OD, and 0.8 mm wall thickness, cut to a length of 10 mm, resulting in an internal volume of 180 μL. The housing 110 is not limited to a particular shape (e.g., oval, rectangular, square). In some embodiments, the shape of the housing 110 is rectangular. The housing 110 is not limited to a particular composition (e.g., plastic, metal, ceramic, or mixture thereof). In some embodiments, the composition of the housing is platinum-cured silicone tubing (Cole Parmer Instrument Company, Vernon Hill, Ill.).

Still referring to FIG. 1, the housing 110 has therein at least one slit 150. The slit 150 is not limited to a particular location within the housing 110. In preferred embodiments, the slit 150 is positioned along a wall of the housing 110. The slit 150 is not limited to a particular length. In some embodiments, the length of the slit 150 extends along an entire side of the housing 110. The slit 150 is not limited to a particular width. In some embodiments, the width of the slit 150 is such that vascular tissue is able to engage the housing 150. The housing 110 is not limited to a particular number of slits 150. In some embodiments, the housing 110 has therein at least three slits 150. In preferred embodiments, as a filtration device 100 is implanted into a subject, vascular tissue (e.g., a tissue flap, an AV loop between the femoral artery and femoral vein, the iliac artery and iliac vein) from the subject engages the housing 110 through the slit 150 resulting in the formation of a capillary bed within the housing 110 (described in more detail below). In preferred embodiments, the filtration device 100 receives and filters impurities from the blood obtained from the capillary bed formed within the housing 110 (described in more detail below).

Still referring to FIG. 1, the housing 110 has therein semi-permeable hollow fibers 160 configured to filter impurities from a subject's blood. The semi-permeable hollow fibers 160 have a front end 170 and a back end 180. The present invention is not limited to a particular type of semi-permeable hollow fiber 180. Suitable semi-permeable hollow fibers 160 useful in accordance with the present invention can be composed of any known biocompatible polymer including CUPROPHAN (a cellulose regenerated by means of the cuprammonium process, available from Enka), HEMOPHAN (a modified CUPROPHAN with improved biocompatibility, available from Enka), CUPRAMMONIUM RAYON (a variety of CUPROPHAN, available from Asahi), BIOMEMBRANE (cuprammonium rayon available from Asahi), saponified cellulose acetate (such as fibers available from Teijin or CD Medical), cellulose acetate (such as fibers available from Toyobo (Nipro), cellulose (such as those regenerated by the modified cupramonium process or by means of the viscose process, available from Terumo or Textikombinat (Pima, GDR) respectively), polyacrylonitrile (PAN), polysulphone, acrylic copolymers (such as acrylonitrile-NA-methallyl-sulfonate copolymer, available from Hospal), polycarbonate copolymer (such as GAMBRONE, a fiber available from Gambro), polymethylmethacrylate copolymers (such as fibers available from Toray), and ethylene vinyl copolymer (such as EVAL, a ethylene-vinyl alcohol copolymer available from Kuraray). In some embodiments, the material of the semi-permeable hollow fibers comprises silicon as silicon nanofabricated membranes (see, e.g., U.S. Patent Publication No. 20040124147, herein incorporated by reference in its entirety). Preferably, polysulphone fibers are used. Other suitable biocompatible fibers are disclosed by, for example, Salem and Mujais, In Dialysis Therapy, ch. 5, 2nd ed., Nissenson and Fine, Eds., Hanley & Belfus, Inc., Pennsylvania, 1993; each of which is herein incorporated by reference in their entireties. The semi-permeable hollow fibers 160 preferably have high hydraulic conductivity, as measured in terms of the ultrafiltration coefficient. Suitably, the ultrafiltration coefficient is greater than 20 mL/hr, Torr, $m^2$ preferably 20-100 mL/hr, Torr, $m^2$. The semi-permeable hollow fibers 160 suitably have a molecular weight cutoff, or pore size, which is, for example, less than or equal to 60,000 g/mol.

The housing 110 is not limited to a particular number of semi-permeable hollow fibers 160. In some embodiments, the housing 110 has therein at least three semi-permeable hollow fibers 160. In some embodiments, the housing 110 has therein at least ten semi-permeable hollow fibers 160. The semi-permeable hollow fibers 160 are not limited to a particular position within the housing 110. In some embodiments, the semi-permeable hollow fibers 160 are positioned within the interior of the housing 110. In preferred embodiments, the semi-permeable hollow fibers 160 are positioned within the interior of the housing 110 such that the semi-permeable housing front end 170 is positioned within the interior of the housing 110, and the semi-permeable housing back end 180 passes through the housing 110 and is positioned outside of the housing 110. In some embodiments, the semi-permeable hollow fiber front end 170 is heat sealed so as to prevent reabsorpiton of filtered materials (e.g., impurities). In preferred embodiments, as blood from a subject is provided into the housing 110 (e.g., from a newly formed capillary bed within the housing 110), the blood passes into the semi-permeable hollow fibers 160. The semi-permeable hollow fibers 160 are configured to filter impurities from a subject's blood while not filtering vital proteins (e.g., albumin). As such, in preferred embodiments, the semi-permeable hollow fibers 160 are configured to filter impurities from a subject's blood in much the same way as a kidney functions.

Still referring to FIG. 1, the conduit 120 is configured to receive filtered material from the housing 110 and pass the filtered material to another component of the present invention. In some embodiments, the conduit 120 passes the filtered material to the reservoir 130. In some embodiments, the conduit 120 passes the filtered material to a renal tubule device containing kidney epithelial cells (see, e.g., U.S. Pat. No. 6,150,164; herein incorporated by reference in its entirety). In some embodiments, the conduit 120 passes the filtered material to a source outside of the subject's body (e.g., a dialysis machine). In some embodiments, the conduit 120 passes the filtered material directly into the subject's ureter. In some embodiments, the conduit 120 passes the filtered material directly into the subject's bladder. In preferred embodiments, the conduit 120 has a conduit front end 190 and a conduit back end 200. In preferred embodiments, the conduit front end 190 receives and encloses the semi-permeable hollow fiber back end 180. The conduit 120 is not limited to a particular composition (e.g., plastic, metal, or mixture thereof). In preferred embodiments, the composition of the conduit 120 is silicone. The conduit 120 is not limited to a particular shape (e.g., oval). In preferred embodiments, the shape of the conduit 120 is tubular. The conduit 120 is not limited to a particular length or width. In preferred embodiments, the size of the conduit 120 is dependent upon the organism for which it is configured. For example, for a rat the dimensions of the conduit are, for example, 1.6 mm ID, 3.2 mm OD, and 0.8 mm wall thickness. The conduit front end 190 is not limited to a particular manner of attachment with the semi-permeable hollow fiber back end 180. In some embodiments, the semi-permeable hollow fiber back end 180 is received into the conduit front end 190 such that no filtered materials are able to pass into the subject's blood stream. In preferred embodiments, materials filtered within the housing 110 are passed into the conduit 120 and passed to the reservoir 130 (described in more detail below).

Still referring to FIG. 1, the reservoir 130 receives filtered materials from the housing 110 and passed through the conduit 120. The reservoir 130 is not limited to a particular size. In preferred embodiments, the size of the reservoir 130 is dependent upon the organism for which it is configured. For example, the internal volume a reservoir 130 configured for a rat is, for example, 0.07 cc. The reservoir 130 is not limited to a particular composition. In preferred embodiments, the composition of the reservoir 130 is silicone. In preferred embodiments, the reservoir 130 has therein a conduit opening 210 for receiving the conduit back end 200. The reservoir 130 is not limited to a particular manner of attachment with the conduit 120. In some embodiments, the conduit back end 200 is glued into an opening within the reservoir 130 such that no filtered materials within the conduit 120 are able to pass into the subject's bloodstream. In some embodiments, the reservoir 130 has therein a vascular access port opening 220 for providing filtered material stored in the reservoir 130 to the vascular access port 140 (described in more detail below).

Still referring to FIG. 1, the vascular access port 140 receives filtered material stored in the reservoir 130 through the vascular access port opening 220. The present invention is not limited to a particular type of vascular access port 140. In preferred embodiments, the vascular access port 140 provides an access point from which the filtered material stored in the reservoir 130 may be withdrawn (e.g., with a syringe).

Figure 12:
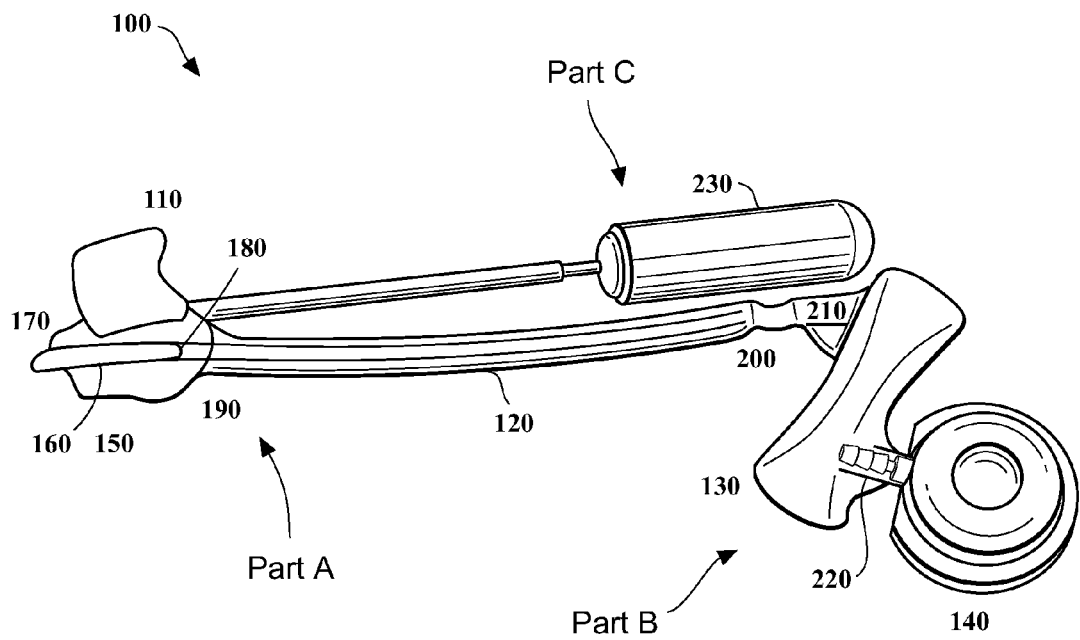
FIG. 12 shows an implantable bioartificial hemofilter device embodiment with the addition of drug delivery pump system. As shown in Part C, the Alzet drug delivery pump is connected via tubing to the inner space of the chamber to deliver growth factors to the area surrounding the hollow fibers.

FIG. 12 shows an additional filtration device 100 of the present invention having a first portion housing 110, a conduit 120 having a front end 190 and a back end 200, a reservoir 130, a vascular access port 140, a second portion housing 150, semi-permeable hollow fibers 160 having a front end 170 and a back end 180, a conduit opening 210 and a vascular access point opening 220. As shown, the filtration device 100 further has a pump 230. The pump 230 is not limited to a particular use. In some embodiments, the pump 230 is used to deliver agents (e.g., pharmaceutical agents) to the second portion housing 150. In some embodiments, the pump 230 is used to deliver agents to the second portion housing 150 over an extended period of time (e.g., 10 minutes, 1 hour, 10 hours, 2 days, 10 days, 6 weeks, etc.). The filtration device 100 is not limited to a particular type of pump 230. Indeed, any type of pump configured for timed release delivery of pharmaceutical agents may be used with the present invention (see, e.g., U.S. Pat. Nos. 6,632,217, 5,024,663, 4,946,456, 4,929,233, 4,913, 702, and U.S. patent application Ser. No. 10/969,753; each herein incorporated by reference in their entireties). In some embodiments, the pump 230 is the Alzet osmotic pump 2004 (Alza, Inc., Mountain View, Calif.) (described in more detail below). The pump 230 is not limited to the delivery of particular pharmaceutical agents. Examples of applicable pharmaceutical agents include, but are not limited to, vascular endothelial growth factors (VEGFs), angiopoietins, platelet-derived growth factor (PDGF), and fibroblast growth factors (FGFs) (see, e.g., Yancopoulos G D, et al., 2000, 407: 242-248; herein incorporated by reference in its entirety). In preferred embodiments, the pump 230 is used to deliver pharmaceutical agents to the second portion housing 150 for the purpose of enhancing capillary development within the filtration devices 100.

Implantable vascular access systems are used extensively in the medical field to facilitate the performance of recurrent therapeutic tasks inside the body of a patient. Such a vascular access system generally includes an implantable vascular access port attached to the proximal end of a vascular catheter. A typical vascular access port has a needle-impenetrable housing that encloses a fluid reservoir that is accessible from the exterior of the access port through a needle-penetrable elastomeric septum. The vascular access port also includes an outlet stem, which projects from the housing and encloses a fluid passageway that communicates with the fluid reservoir. The distal end of the catheter is mechanically coupled to the vascular access port in fluid-tight communication with the fluid reservoir using the outlet stem. An example of a vascular access port is described in, for example, U.S. Pat. No. 6,213, 973, herein incorporated by reference in its entirety. In some embodiments, the vascular access port is developed by Access Technologies, Skokie, Ill.

It is contemplated that the filtration devices of the present invention may be combined within various kits or system embodiments. For example, the kits or systems may comprise the filtration devices of the present invention or various parts of the filtration devices (e.g., the housing, conduit, reservoir). Additionally, the kits or systems may be combined with various surgical instruments necessary for implanting the filtration device into an organism.

It is contemplated that the filtration devices of the present invention may be used in the treatment of any kind of disease or condition resulting in a diminished ability to filter impurities from a bodily fluid (e.g., acute kidney failure, ESRD, renal disease).

EXAMPLES

Example 1

This example describes the in vivo implantation of a filtration device of the present invention into a rat. A 3-cm-long skin incision was made in the left groin of adult Fisher 344 male rats weighing approximately 300 grams each. The femoral artery and vein were dissected free from surrounding structures under an operating microscope, from the inguinal ligament to their bifurcations at the knee. Vascular branches were cauterized and divided. The housing containing the semi-permeable hollow fibers was implanted around the femoral vessels by passing them through the longitudinal slit in the housing. A separate 3-cm incision was made on the ipsilateral back of the animal for implanting the reservoir of the device. The distal end of conduit attached to the housing was transposed to the back of the animal through a subcutaneous tunnel. The vascular access port was accessed percutaneously using a 25-gauge needle, and the system was flushed with 3-4 cc of saline and aspirated to create negative pressure within the reservoir. Fluid accumulating in the reservoir was collected at specified times by insertion of a needle into the vascular access port.

Three groups of animals receiving implants were tested in the first set of experiments utilizing the axial vascular design. Group 1 utilized ten polyarylethersulfone semi-permeable hollow fibers (MW cut off<55 kDa, OD=250 µm, ID=215 µm; Amicon Corp., Manchester, Mass.). Groups 2 and 3 utilized three polysulfone HP100 semi-permeable hollow fibers (MW≦100 kDa, OD=625 µm, ID=555 µm; Amicon Corp., Manchester, Mass.). Group 3 additionally utilized minced renal cortical tissue within alginate aggregates of approximately 250 µm in diameter placed in the inner volume of the polycarbonate capsule. This renal tissue was obtained from a syngeneic litter mate. The semi-permeable hollow fiber surface area was approximately 33 percent greater in group 1 compared to groups 2 and 3.

Each animal group consisted of three Fisher 344 male rats and was monitored for 6 weeks following implantation. After the first week, the vascular access port was tapped three times a week for fluid measured for volume, BUN, total protein, and albumin concentrations. Serum from these rats was collected at the end of the fourth and sixth weeks following implantation. Comparisons of the ratios of serum to capsular fluid concentrations were assessed.

Figure 2:
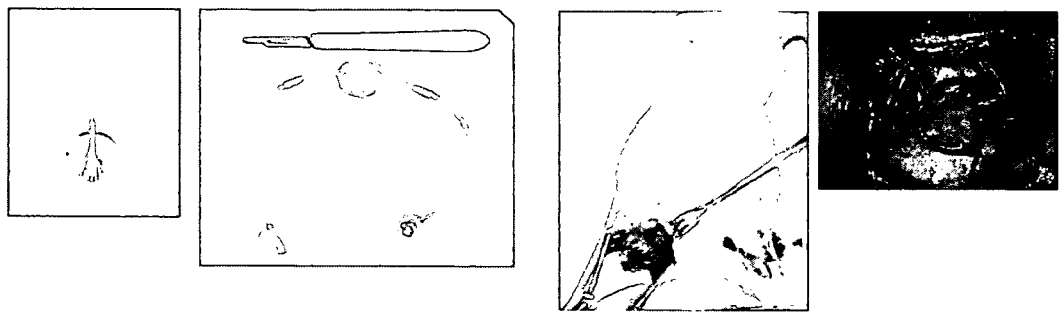
FIG. 2 shows a filtration device implanted into a rat.
Figure 2:

An AV loop was created between femoral artery and vein in the rat groin, utilizing a 2-cm interpositional vein graft harvested from the contralateral femoral vein. The AV loop was then placed within a cylindrical polycarbonate housing with an opening for the pedicle (0.5 cc internal volume) (see, FIG. 2). FIG. 2 shows the housing, reservoir, and vascular access port utilizing the arteriovenous (AV) loop approach. The left panel of FIG. 2A depicts the semi-permeable hollow fibers within the housing. The right panel of FIG. 2A demonstrates the entire unit. The left panel of FIG. 2B demonstrates the exposed femoral area of the rat in which, as shown in the right panel, the AV loop between the femoral artery and vein has been constructed. FIG. 2C shows the whole unit after implantation. FIG. 2D shows a low-power image of the explant tissue after 6 weeks of maturation.

The filtration devices were removed and put in methanol. The mid-portion of each sample was selected and subjected to processing and paraffinization by standard procedures. Sections were cut with a microtome (5 µm) and stained with hematoxylin and eosin (H&E). To visualize and evaluate neovascularization, endothelial cells were stained with antibodies raised against von Willebrand factor. Sections were deparaffinized and rehydrated. They were then incubated with proteinase K solution at 37° C. for 20 minutes. After Proteinase K Epitope Retrival, they were incubated with normal goat serum blocking solution for 30 minutes, followed by Rabbit Anti-Human von Willebrand Factor (1:500, DakoCytomation, Carpinteria, Calif.) as a primary antibody for 1 hour, peroxidase blocking solution for 10 minutes, and Goat Anti-Rabbit IgG (1:500, Vector Laboratories, Burlingame, Calif.) as a secondary antibody for 30 minutes. In the detection process, they were incubated with HRP-Streptavidine for 30 minutes and finally DAB peroxidase substrate solution for 10 minutes. Endothelial cells of capillaries and larger vessels were visualized in the tissue as a brown precipitate. For morphometric assessment, only the stained vessels inside the housing but neither the main original artery nor vein were considered. The digital images were taken from Leica DMIRB microscope at 20 magnification using a RT slider digital camera (type 2.3.1; Diagnostic Instruments, Los Angeles, Calif.) with Spot software (Diagnostic Instruments Inc.). The entire inside-housing tissue was evaluated with digitized images obtained for morphometric analysis. The vessels were manually identified and cross-sectional area delineated using Photoshop Program (Adobe Systems, Mountain View, Calif.). Subsequently, the vascular density and cross-sectional area were analyzed using Scion Image Program (Scion Corporation, Frederick, Md.) in which the measured pixel sizes of each vessel cross section and tissue area were converted to square microns. The vascular analysis data of each device sample was derived from the summation of the values within the digitized images.

The data were presented as mean ±SE and analyzed using the SPSS program (version 11.0; SPSS Inc., Chicago, Ill.). Differences in UF volumes and vascular parameters among groups were analyzed using one-way analysis of variance (ANOVA) followed by LSD (least significant difference) post hoc tests for multiple group comparisons. Subgroup analysis between two groups was examined by Student's two-tailed t-test. Correlation between UF volumes and vascular parameters were explored and shown as R value. For permselectivity analysis, ultrafiltration/serum ratio of urea nitrogen, total protein, and albumin of all implants were tested using Student's two-tailed t-test. All significances were taken at a value of $P<0.05$.

Example II

This example describes the vascular density (VD) and percent of cross-sectional vascular area to total tissue area (PVA) for rats with an implanted filtration device. At 6 weeks all housings were explanted and examined. In all cases, new tissue formation extended into the entire capsular volume and surrounded the intact semi-permeable hollow fibers. The group 3 tissues revealed the presence of alginate, which occupied a large component of the housing. Representative microscopic views from each group are depicted in FIGS. 3, 4, and 5.

Figures 3, 4, 5:
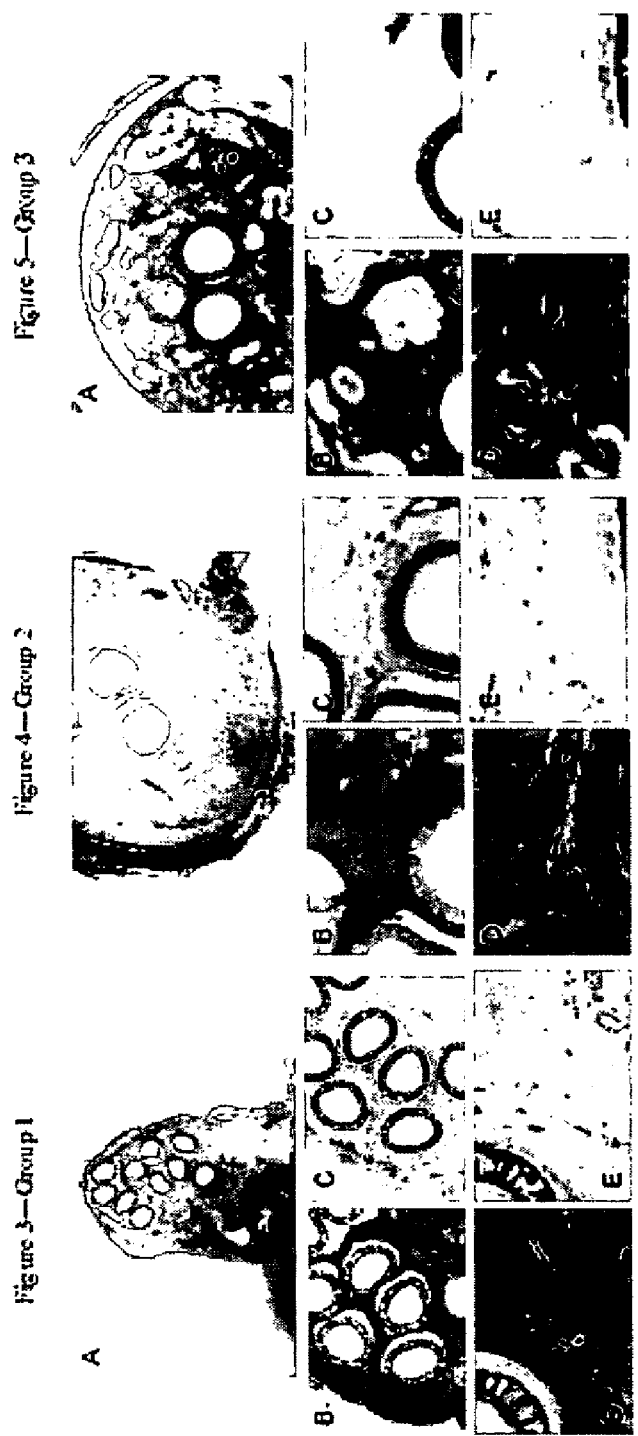
FIG. 3 shows explants from rats with an implanted filtration device.
FIG. 4 shows explants from rats with an implanted filtration device.
FIG. 5 shows explants from rats with an implanted filtration device.

Panel A of FIGS. 3, 4 and 5 is a low-power H & E section (40× magnification) of the implant with new tissue formation surrounding the semi-permeable hollow fibers. Of note, the artery and vein pedicle is shown in the lower left region of the histologic specimen. Panels B and D of FIGS. 3, 4 and 5 are higher power views (100× and 200×, respectively) of the H & E section in panel A. Panels C and E of FIGS. 3, 4 and 5 are corresponding sections stained with vWF antibody, which identifies endothelial cells. The presence of capillaries are readily apparent in all sections.

Figure 6:
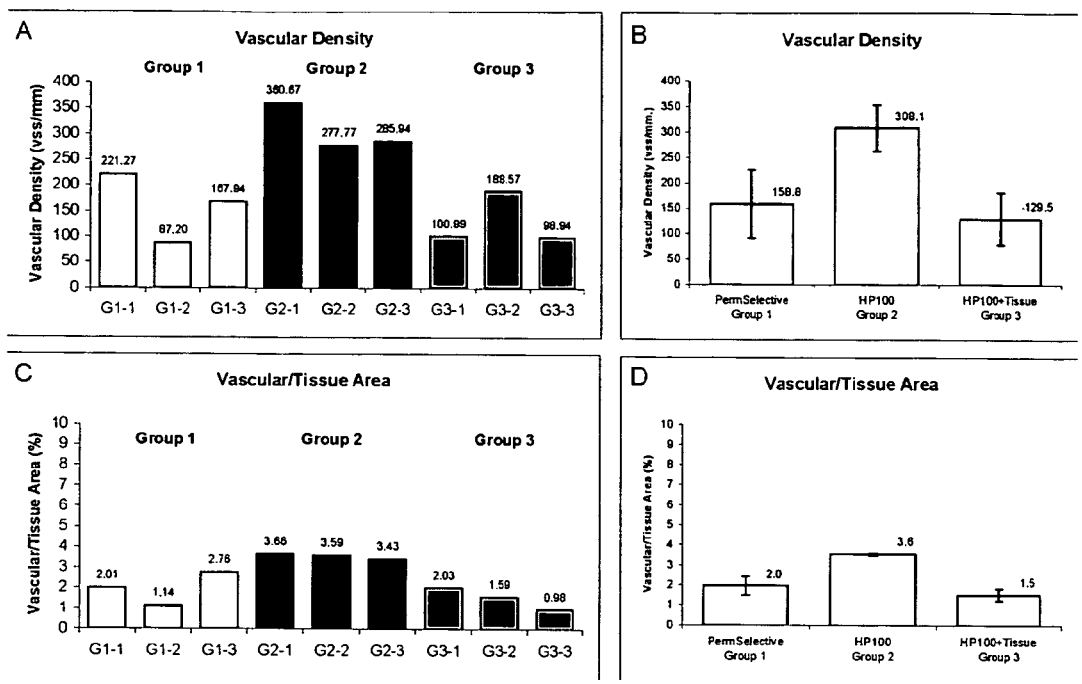
FIG. 6 shows the vascular density (VD) and percent of cross-sectional vascular area to total tissue area (PVA) for rats with an implanted filtration device.

The VD and PVA of each implant and the mean of each group are shown in FIG. 6. Panels A and C of FIG. 6 depict the individual vascular density and vascular/tissue area values for each of the three rats in each group. Panels B and D of FIG. 6 summarize the mean ±S.E. values of the vascular measures in panels A and C for each of the three groups.

There were significant differences in the VD among the three groups (mean ±S.E.: 158.8±39.0, 308.1±26.4, and 129.5±29.5 vessels/mm$^2$ for groups 1, 2, and 3, respectively, p=0.02), with group 2 significantly higher than groups 1 and 3. Correspondingly, the percent vascular area was significantly different among the three groups, with group 2 significantly higher than the others (2.0±0.5, 3.6±0.1, and 1.5±0.3% for groups 1, 2, and 3, respectively, p=0.01).

Figure 7:
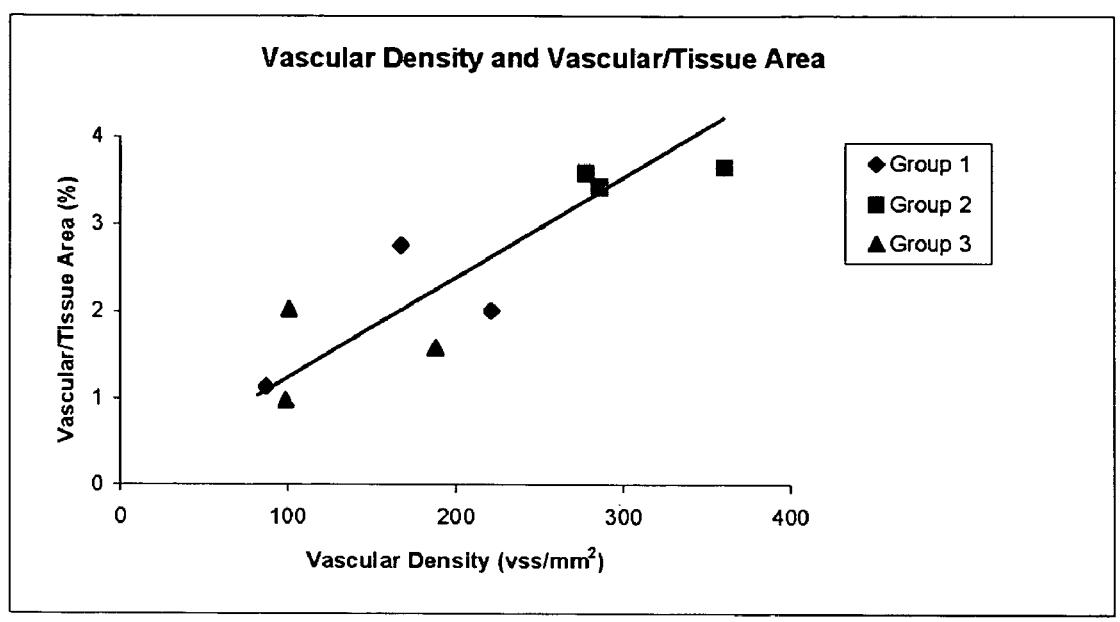
FIG. 7 shows the relationship between VD and PVA for rats with an implanted filtration device.
Figure 8:
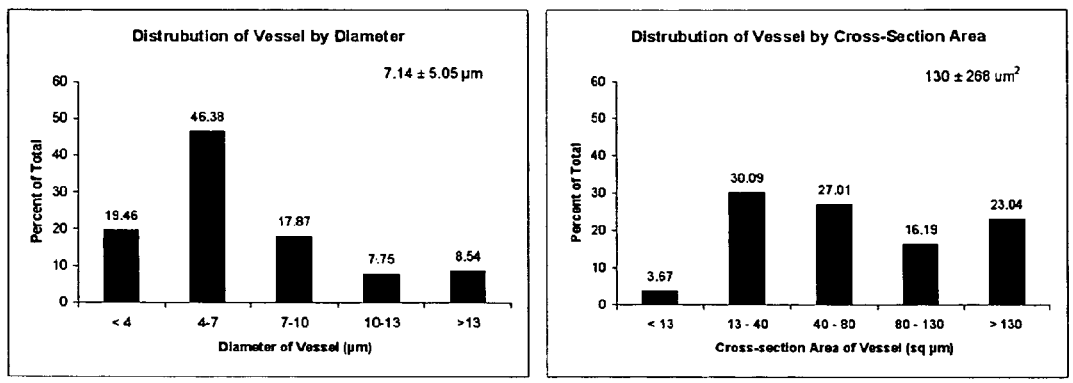
FIG. 8 shows the correlation between VD and PVA for rats with an implanted filtration device.
Figure 8:
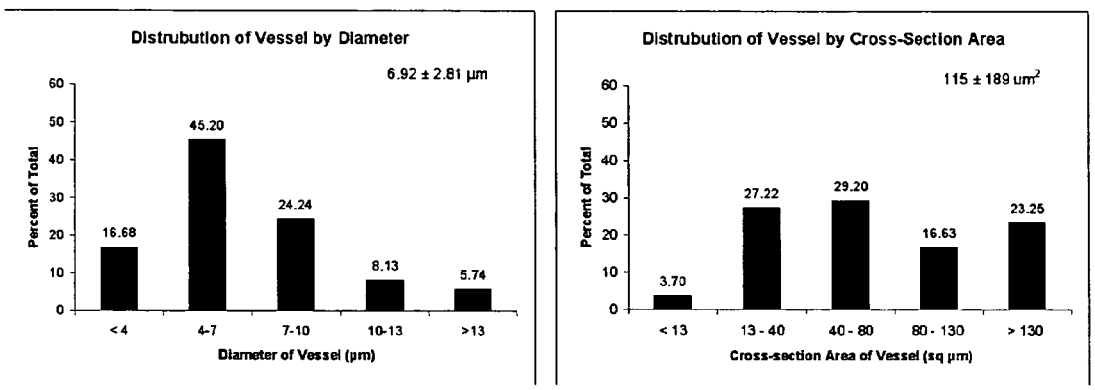
Figure 8:
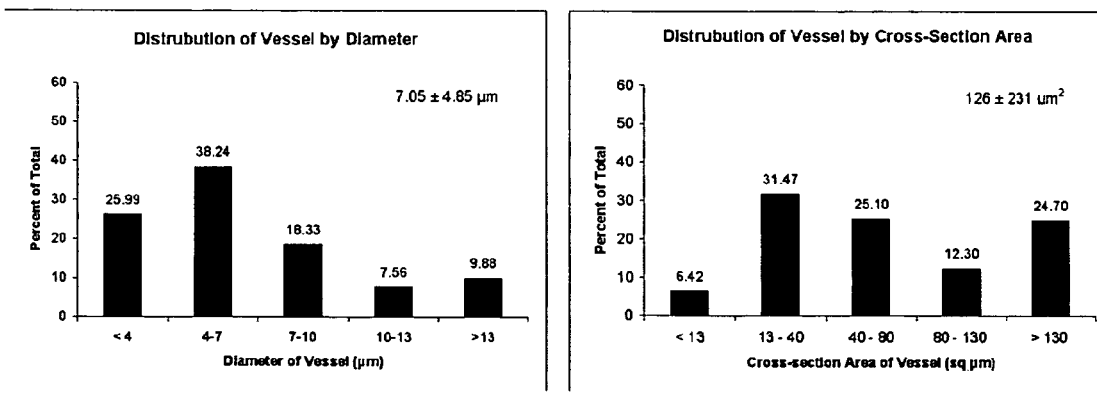

A direct correlation between the VD and PVA of each tissue sample was also demonstrated (R=0.867, p<0.01; FIG. 7). The distribution of vessel diameters and vascular cross-sectional areas in each group is depicted in FIG. 8. The distribution patterns among the three groups were similar.

The rate of fluid formation emanating from the filtration device was determined by (1) vascular density (capillary surface area), (2) semi-permeable hollow fiber surface area, (3) hydraulic permeability of the semi-permeable hollow fiber membranes, and (4) the hydraulic pressure difference driving convective fluid transport. Assuming for the various groups that the third and fourth components within the implants are similar, the major determinants of fluid formation in these experiments are vascular density and semi-permeable hollow fiber surface area.

Figure 9:
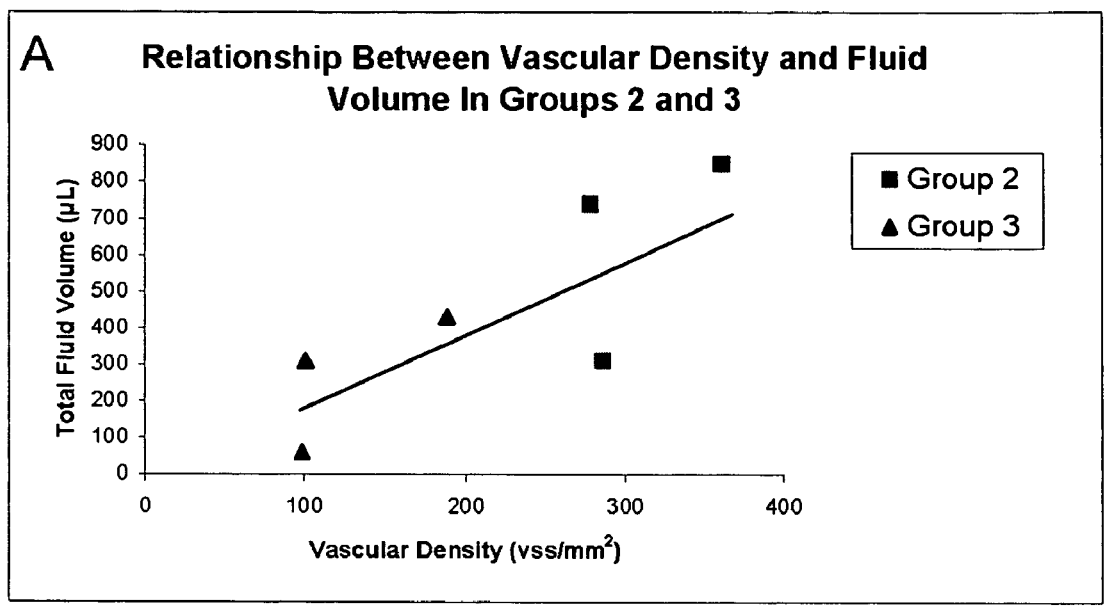
FIG. 9 shows the relationship between VD and PVA for rats with an implanted filtration device.
Figure 9:
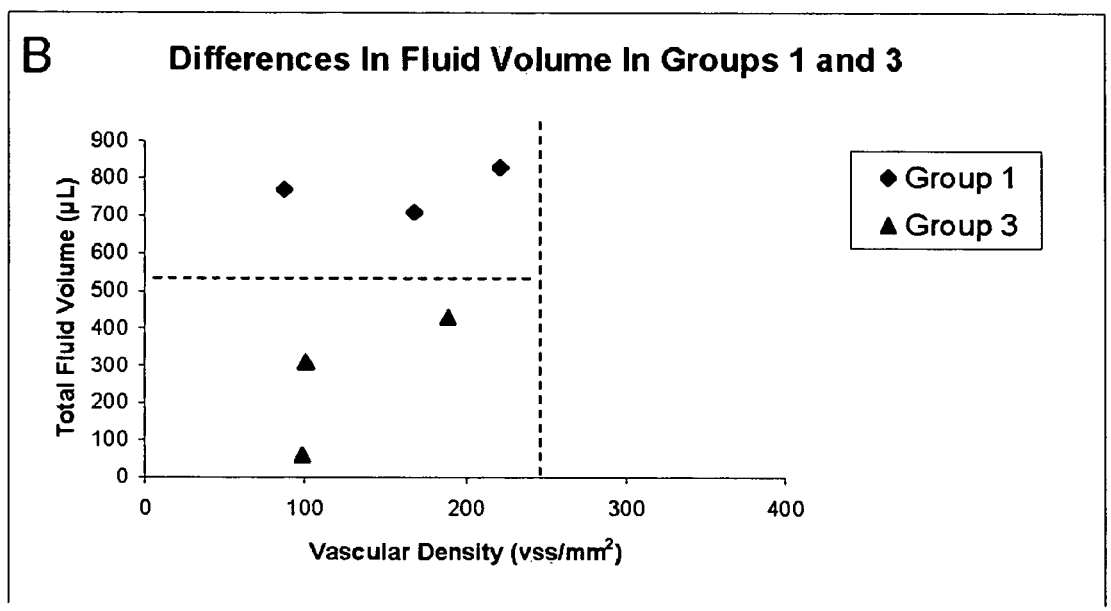
Figure 10:
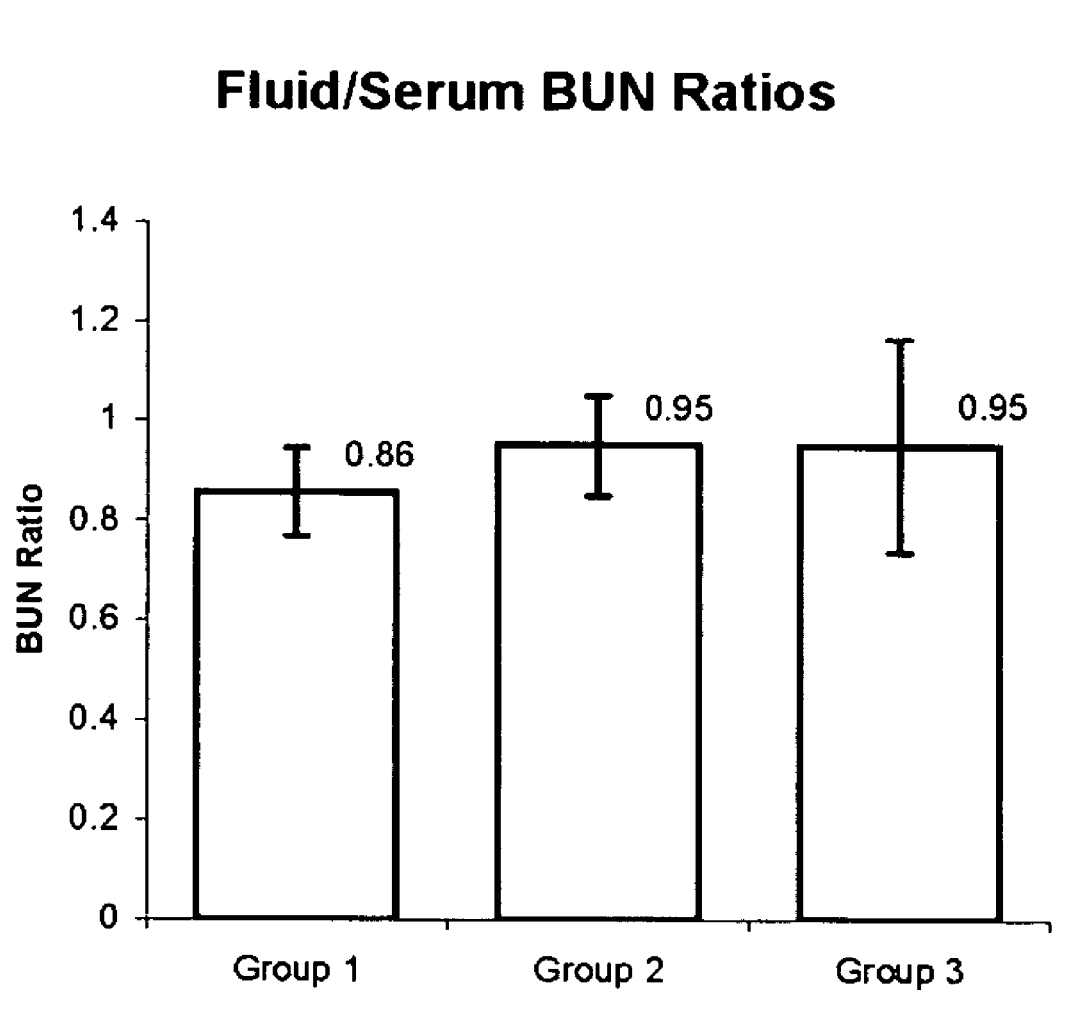
FIG. 10 shows implant fluid to serum BUN ratios for rats with implanted filtration devices.
Figure 11:
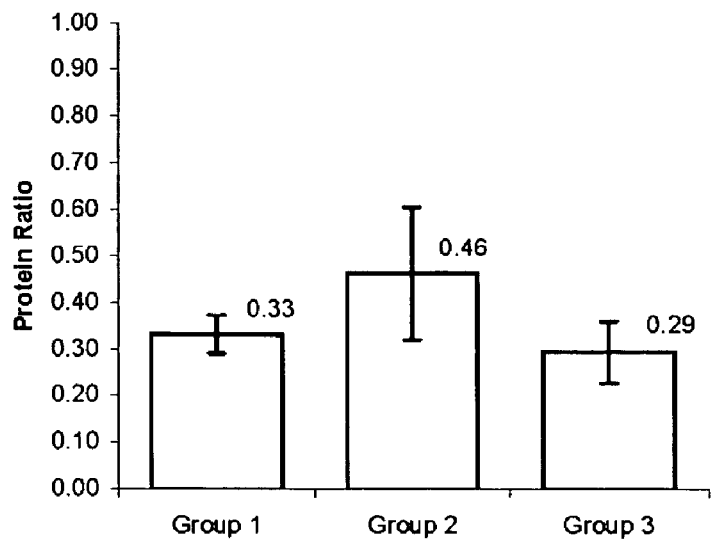
FIG. 11 shows implant fluid to serum protein ratios and serum albumin ratios for rats with implanted filtration devices.
Figure 11:
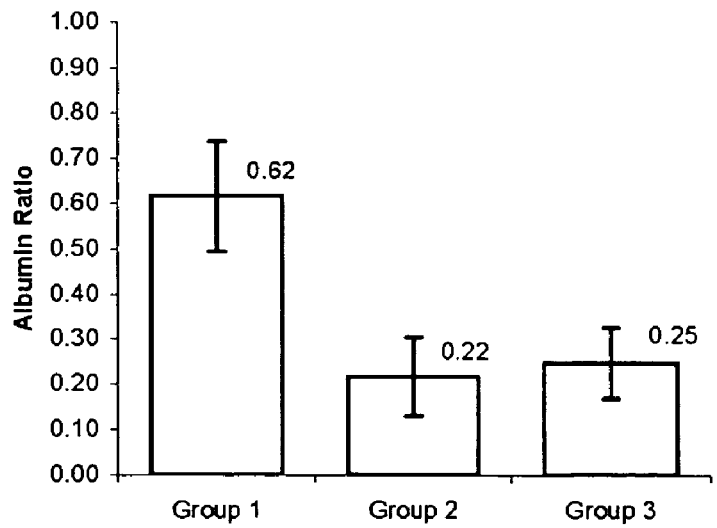

To determine these relationships, the fluid volume over the last 4-week time course of the implants was determined and compared to vascular density for the two groups with similar semi-permeable hollow fiber surface areas (groups 2 and 3) as well as the comparison of different semi-permeable hollow fiber surface areas (groups 1 and 2) which had similar vascular densities. The last 4-week volumes were used because the implants matured over the first 14 days after implantation; thus, these volumes were more reflective of a steady-state performance. FIG. 9 shows correlations among the various groups between vascular density and fluid volumes. Panel A of FIG. 9 depicts the correlation between vascular density and fluid volume formation in implants with similar semi-permeable hollow fiber membrane surface areas but varying vascular densities (r=0.812, p<0.05). Panel B of FIG. 9 displays the differences in fluid volume in implants with different semi-permeable hollow fiber membrane surface areas but similar vascular densities (p<0.01). As depicted in FIG. 9A, there was a direct correlation between vascular density and fluid formation (r=0.812, p<0.05). The fluid volumes in groups 1 and 3 were significantly different (p<0.01) with fluid volumes of 770±35 and 267±109 μL/4 weeks, respectively.

The permselectivity of the filtration device permits small solute transfer as represented by BUN, but retard large proteins. In this regard, FIGS. 10 and 11 demonstrate the ratios of the implant fluid to serum values for BUN and total protein, respectively. The mean fluid/serum BUN ratio results were 0.86±0.09 for group 1, 0.95±0.10 for group 2, and 0.95±0.21 for group 3, respectively, values not significantly different from 1.00 (p>0.05). In contrast to BUN, a significant difference (p<0.01) from 1.00 was seen in all groups for total protein and albumin. The mean fluid/serum protein ratios were 0.33±0.04, 0.46±0.14, and 0.29±0.07, and the mean fluid/serum albumin ratios were 0.62±0.12, 0.22±0.09, and 0.25±0.08 for groups 1, 2, and 3, respectively.

Example III

This example demonstrates the effect of angiogenic factor infusion on implant characterisitics. In an attempt to increase neovascularization and, thereby, increase fluid formation, additional experiments utilized delivery of angiogenic growth factors within the chamber. The combination of the growth factors PDGF and VEGF has been shown to produce a mature, durable vascular bed in an animal model (see, e.g., Richardson T P, et al., 2001, Nat. Biotechnol. 19:1029-1034; herein incorporated by reference in its entirety). The implants for these groups were fabricated using three HP100 hollow fibers per chamber, as described in Examples I and II. An Alzet osmotic pump 2004 (Alza, Inc., Mountain View, Calif.) was attached to each implant (FIG. 12), with its outflow directed into the lumen of the chamber via a small, distally perforated silicone tube. Two groups of animals were used. Group 4 (n=12) received implantation of bioartificial hemofilter devices and pumps containing sham carrier solution (0.1% rat serum albumin and 76 μM acetic acid in normal saline). In Group 5 (n=12), the pumps were pre-filled with PDGF$_{BB}$ (R&D Systems, Minneapolis, Minn., #520-BB-50) and VEGF-164 (Pro Spec-Tany TechnoGene, Ltd., Rehovot, Israel, #CYT-392) for delivery at rates of 2.7 ng/d and 23 ng/d, respectively, for 28 consecutive days, at a rate of 0.25 μL/h. Fluid was obtained from the implants two to three times a week after the first two weeks. Fluid production volumes were measured, and various samples were analyzed for BUN, protein, and albumin. Six animals from each group were sacrificed at four weeks, three animals at six weeks, and three animals at nine weeks. Serum from each animal was obtained at the time of sacrifice and evaluated for BUN, total protein, and albumin. At sacrifice, the implants were harvested and newly generated tissue from the implants was processed and analyzed.

Figure 13A:
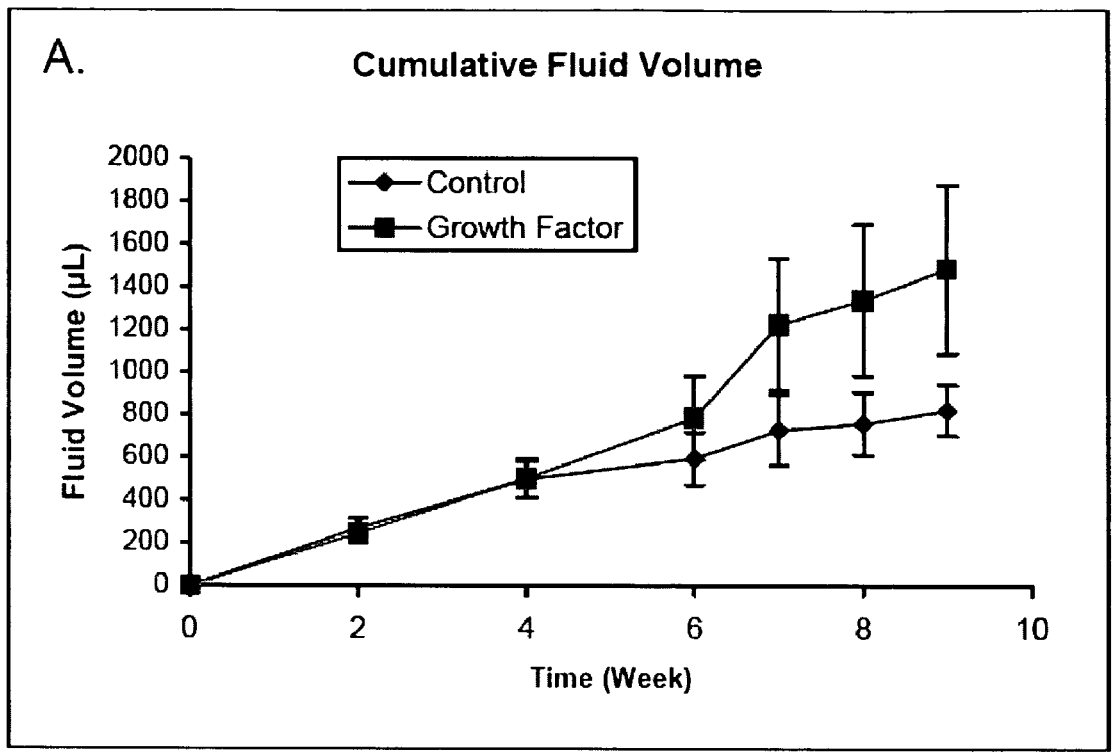
FIG. 13 shows implant fluid production. A) Cumulative fluid volumes in control and growth factor treated groups for all animals sacrificed at 4 (n=12 control, 10 treated), 6 (n=6 control, 6 treated) or 9 (n=3 control, 3 treated) weeks. B) Last 4- and last 2-week (prior to sacrifice) fluid production volumes for animals sacrificed at weeks 4, 6 and 9. Evident is the significant increase in cumulative fluid volume for growth factor treated animals after 4 weeks following implantation.
Figure 13B:
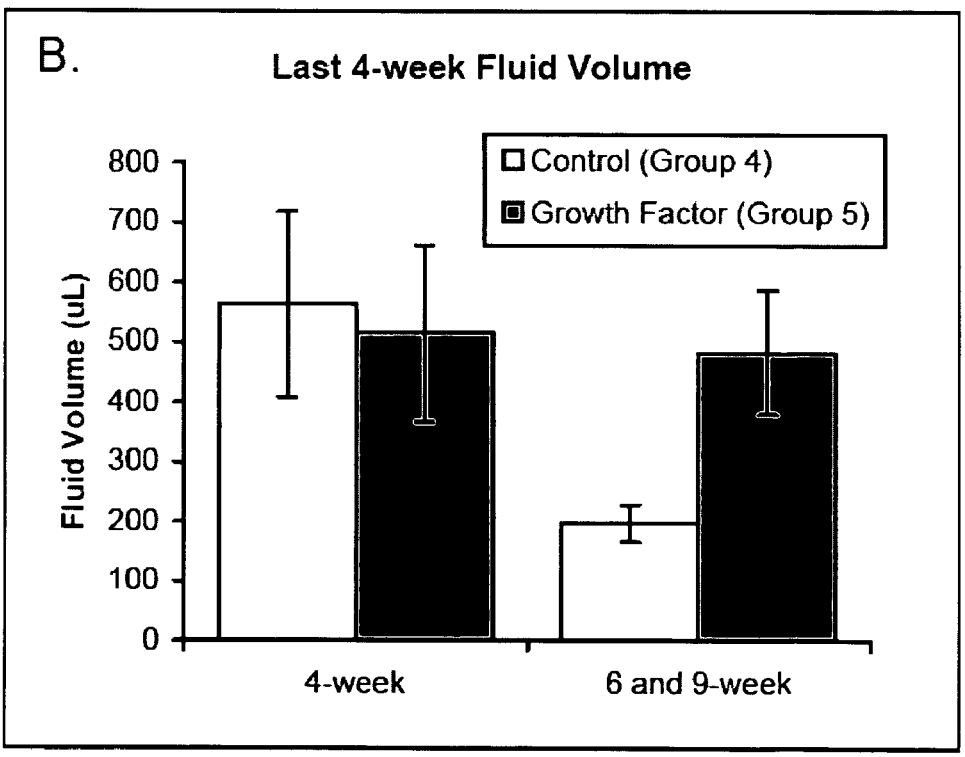
Figure 14:
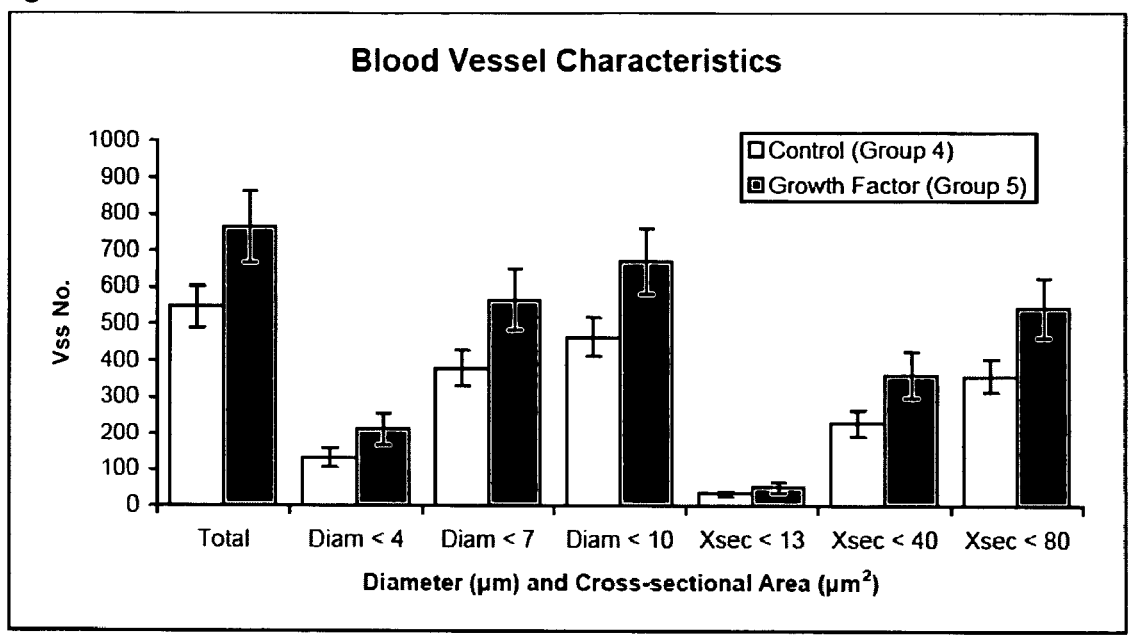
FIG. 14 show percentile distribution of newly formed vessels by diameter and cross-sectional area in Groups 4 (control) and 5 (GF infusion). The increase in fluid formation in the growth factor treated group was associated with an absolute increase in the number of vessels, especially smaller vessels with diameters<10 μm ($p=0.052$) or cross-sectional area<80 μm2 ($p=0.047$) compared to control animals.

Four weeks of infusion of angiogenic factors increased the implant fluid volume compared to controls. FIGS. 13A and B demonstrate the volume production of Groups 4 (control) and 5 (GF infusion) for all animals at 4, 6, 7, 8, and 9 weeks. This increase in fluid volume was demonstrated at all time points after the growth factor infusion was stopped at four weeks. Evaluation of the last 4-week fluid volumes of week 6 and 9 animals demonstrated a significant (p<0.025) increase in volumes for the infused animals. Histomorphometric analysis did not demonstrate differences between the two groups for vascular density or vascular area to tissue area. This increase in fluid formation, however, was associated with an absolute increase in the number of vessels, especially smaller vessels with diameters<10 μm (p=0.052) and cross-sectional area <80 μm2 (p=0.047) in the angiogenic factor treated animals compared to control animals as depicted in FIG. 14.

Similar to the prior experiments, the fluid volume was characteristic of an ultrafiltrate. The fluid-to-serum BUN ratios were not different from 1.0, with the control group averaging 1.09±0.13 and the angiogenic factor group averaging 1.32±0.18. The fluid-to-serum protein ratios, however, were significantly different from 1.00 (p<0.001), with protein ratios of 0.33±0.03, and 0.29±0.06 for control and growth factor groups, respectively.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating renal failure in a subject, comprising:
   (a) providing a device comprising (i) a housing defining at least one opening and (ii) a plurality of semi-permeable hollow fibers disposed within the housing; and
   (b) positioning a tissue flap or an arteriovenous loop from the subject in the device through the opening so that the tissue flap or the arteriovenous loop forms a capillary bed within the housing that permits impurities in the blood of the subject to pass from the capillary bed and into the hollow fibers.

2. The method of claim 1 further comprising introducing into the device an exogenous growth factor for enhancing capillary bed formation within the housing.

3. The method of claim 1, wherein least one growth factor is selected from the group consisting of platelet-derived growth factors, vascular endothelial growth factors, and fibroblast growth factors.

4. The method of claim 1, wherein the arteriovenous loop is formed between a femoral artery and a femoral vein of the subject.

5. The method of claim 1 further comprising the step of implanting the device into the subject.

6. The method of claim 1, wherein the impurities flow into a reservoir in communication with the hollow fibers.

* * * * *